United States Patent
Chen et al.

(10) Patent No.: US 10,039,697 B2
(45) Date of Patent: *Aug. 7, 2018

(54) DENTIFRICE COMPOSITIONS HAVING IMPROVED FLUORIDE ION STABILITY OR FLUORIDE UPTAKE

(71) Applicant: The Procter & Gamble Company, Cincinnati, OH (US)

(72) Inventors: Haijing Chen, Beijing (CN); Wenying Gao, Beijing (CN); Ross Strand, Singapore (SG); Gang Wu, Beijing (CN); Hongmei Yang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 47 days.

This patent is subject to a terminal disclaimer.

(21) Appl. No.: 14/830,839

(22) Filed: Aug. 20, 2015

(65) Prior Publication Data

US 2016/0317406 A1  Nov. 3, 2016

(51) Int. Cl.
| | | |
|---|---|---|
| *A61K 8/34* | (2006.01) | |
| *A61K 8/37* | (2006.01) | |
| *A61K 8/73* | (2006.01) | |
| *A61K 8/21* | (2006.01) | |
| *A61Q 11/00* | (2006.01) | |
| *A61K 33/10* | (2006.01) | |
| *A61K 8/24* | (2006.01) | |
| *A61K 8/19* | (2006.01) | |
| *A61K 33/06* | (2006.01) | |

(52) U.S. Cl.
CPC ................. *A61K 8/24* (2013.01); *A61K 8/19* (2013.01); *A61K 8/34* (2013.01); *A61K 33/06* (2013.01); *A61K 33/10* (2013.01); *A61Q 11/00* (2013.01); *A61K 8/345* (2013.01); *A61K 2800/28* (2013.01)

(58) Field of Classification Search
CPC ... A61K 8/24; A61K 8/19; A61K 8/73; A61K 8/731; A61K 8/39; A61K 8/37; A61K 8/345; A61Q 11/00

See application file for complete search history.

(56) References Cited

U.S. PATENT DOCUMENTS

| | | |
|---|---|---|
| 3,119,743 A | 1/1964 | Ericsson |
| 4,046,872 A | 9/1977 | Mitchell et al. |
| 4,283,385 A | 8/1981 | Dhabhar et al. |
| 4,565,691 A | 1/1986 | Jackson |
| 4,678,662 A | 7/1987 | Chan |
| 4,701,319 A | 10/1987 | Woo |
| 4,828,849 A | 5/1989 | Lynch et al. |
| 5,939,052 A | 8/1999 | White, Jr. et al. |
| 6,106,811 A | 8/2000 | Gibbs |
| 6,159,446 A | 12/2000 | Randive et al. |
| 6,696,045 B2 | 2/2004 | Yue et al. |
| 6,759,876 B2 | 7/2004 | Inoue et al. |
| 7,648,363 B2 | 1/2010 | Oniki et al. |
| 8,007,771 B2 | 8/2011 | Ramji et al. |
| 2002/0001569 A1 | 1/2002 | Dromard |
| 2003/0072721 A1 | 4/2003 | Riley et al. |
| 2003/0095931 A1 | 5/2003 | Stier |
| 2004/0120902 A1 | 6/2004 | Wernett et al. |
| 2004/0131560 A1 | 7/2004 | Corcoran et al. |
| 2005/0084460 A1* | 4/2005 | Winston .................. A61K 8/19 424/49 |
| 2006/0134020 A1 | 6/2006 | Robinson et al. |
| 2006/0159631 A1 | 7/2006 | Buch et al. |
| 2007/0231278 A1 | 10/2007 | Lee et al. |
| 2008/0230298 A1 | 9/2008 | Buch et al. |
| 2009/0136584 A1 | 5/2009 | Hosoya et al. |
| 2009/0202453 A1* | 8/2009 | Waterfield ............... A61K 8/19 424/52 |
| 2009/0269287 A1 | 10/2009 | Berta |
| 2010/0086498 A1 | 4/2010 | Haught et al. |
| 2012/0189561 A1 | 7/2012 | Randive et al. |
| 2013/0064779 A1 | 3/2013 | Yamane et al. |
| 2013/0280182 A1 | 10/2013 | Burgess et al. |
| 2013/0344120 A1 | 12/2013 | Scott et al. |

FOREIGN PATENT DOCUMENTS

| | | |
|---|---|---|
| CN | 101690699 A | 4/2010 |
| CN | 102283795 A | 12/2011 |
| CN | 102283794 B | 7/2013 |
| EP | 2057978 A1 | 5/2009 |
| KR | 2002/0054045 A | 7/2002 |
| KR | 2012/0042399 A | 5/2012 |
| WO | WO2005058364 A2 | 6/2005 |
| WO | WO 2007/122146 A1 | 11/2007 |
| WO | WO2008041055 A1 | 4/2008 |
| WO | WO 2007/076001 A3 | 12/2008 |
| WO | WO2008005548 A3 | 7/2009 |
| WO | WO2010114546 A1 | 10/2010 |
| WO | WO2011031807 A3 | 3/2011 |
| WO | WO2011157497 A1 | 12/2011 |
| WO | WO 2013/034421 A2 | 3/2013 |
| WO | WO 2013/094312 A1 | 6/2013 |
| WO | WO2015094152 A1 | 6/2015 |
| WO | WO2015094154 A1 | 6/2015 |

OTHER PUBLICATIONS

Pearce, et al. "The Effect of pH, Temperature and Plaque Thickness on the Hydrolysis of Monofluorophosphate in Experimental Dental Plaque", Caries Research, vol. 37, pp. 178-184, Feb. 1, 2003.
PCT International Search Report—5 pages.
EP 15793035 (P&G Case No. AA941M) Supplementary European Search Report dated Oct. 20, 2017.
PCT/CN2014/077427 (P&G Case No. AA930) International Search Report and Written Opinion dated Feb. 17, 2016.

(Continued)

*Primary Examiner* — Lezah Roberts
(74) *Attorney, Agent, or Firm* — Parker D. McCrary; Alexandra S. Anoff

(57) ABSTRACT

Certain dentifrice compositions having a pyrophosphate ion and an alkaline pH have improved fluoride ion stability or fluoride uptake.

18 Claims, No Drawings

(56) References Cited

OTHER PUBLICATIONS

PCT/CN2014/077536 (P&G Case No. AA935) International Search Report and Written Opinion dated May 15, 2014.
PCT/CN2014/077527 (P&G Case No. AA939) International Search Report and Written Opinion dated Feb. 10, 2015.
All Office Actions, U.S. Pat. No. 9,687,427.
All Office Actions, U.S. Appl. No. 14/633,389.
All Office Actions, U.S. Pat. No. 9,498,416.
All Office Actions, U.S. Appl. No. 15/294,855.
All Office Actions, U.S. Appl. No. 14/634,969.
All Office Actions, U.S. Appl. No. 14/635,234.
All Office Actions, U.S. Appl. No. 14/700,182.
All Office Actions, U.S. Appl. No. 14/830,815.
All Office Actions, U.S. Appl. No. 14/634,993.
All Office Actions, U.S. Appl. No. 14/830,831.
All Office Actions, U.S. Appl. No. 14/634,949.
All Office Actions, U.S. Pat. No. 9,364,419.
All Office Actions, U.S. Appl. No. 15/150,486.
All Office Actions, U.S. Appl. No. 14/682,141.
All Office Actions, U.S. Appl. No. 14/682,146.
All Office Actions, U.S. Appl. No. 14/700,196.
All Office Actions, U.S. Appl. No. 14/736,352.

* cited by examiner

DENTIFRICE COMPOSITIONS HAVING IMPROVED FLUORIDE ION STABILITY OR FLUORIDE UPTAKE

CROSS REFERENCE TO RELATED APPLICATIONS

This Application claims the benefit of Application Serial No. CN2015/077636 filed Apr. 28, 2015 and Application Serial No. CN2014/077555 filed May 15, 2014.

FIELD OF THE INVENTION

The present invention relates to dentifrice compositions having improved sustained monofluorophosphate ion levels overtime.

BACKGROUND OF THE INVENTION

Dentifrice compositions are well known for dental and oral hygiene care. High carbonate (e.g., >25 wt %) formulation chassis are cost effective for many markets and consumers. Fluoride and its benefits are well known (e.g., helping to prevent tooth decay). Sodium monofluorophosphate as fluoride ion source is also generally a well known way to provide fluoride benefits through dentifrice. However, there is a continuing need to provide dentifrice formulations that maximize available sodium monofluorophosphate, especially as formulations age (e.g., through distribution channels and on shelf).

SUMMARY OF THE INVENTION

The present invention is based on a surprising discovery on the role of forming and maintaining the specific fluoride species whereby the degradation of the monofluorophosphate ion is significantly reduced. This is achieved through the use of calcium chelating agents, in combination a high carbonate and/or high water dentifrice compositions that create the desired fluoride species with both improved stability and performance over the shelf life of the product. Under alkali conditions the monofluorophosphate ions will dissociate accordingly to liberate free fluoride ions that complex with surface $Ca^{2+}$ ions on the calcium carbonate particle, further to that sodium monofluorophosphate may undergo slow hydrolysis.

The use of pyrophosphate salts, alkali metal silicates or mixtures thereof can aid in reducing the formation of undesirable calcium fluoride within a calcium carbonate and sodium monofluorophosphate containing dentifrice compositions. The present invention identifies a means to deliver and maintain the desired fluoride species, whereby firstly there is minimal degradation of the monofluorophosphate ion species, and secondly monofluorophosphate ions that undergo degradation are maintained as free fluoride ion source, resulting in improved stability and performance in fluoride uptake. Too much calcium chelating agent, e.g., pyrophosphate salts can create consumer negatives around irritation of the soft tissue.

Another surprising observation is that soluble fluoride ion stability is increased in high carbonate dentifrice formulations with the use of carrageenan.

Yet a further surprising discovery is the role of alkaline pH, especially those formulations having a pH above 8.3, to improve the equilibrium speciation that results in improved stability of monofluorophosphate ions. Without wishing to be bound by theory, the higher pH allows the equilibrium speciation of the more preferred fluoride species that have both an improved stability profile and improved efficacy.

One aspect of the invention provides a dentifrice composition comprising: (a) 25% to 60%, preferably 27% to 47%, of a calcium-containing abrasive by weight of the composition, preferably wherein the calcium-containing abrasive comprises calcium carbonate composition; (b) 0.0025% to 4.0%, preferably from 0.19% to 3.8% sodium monofluorophosphate by weight of the composition; (c) 0.001% to 4% calcium chelating agent by weight of the composition, preferably wherein the calcium chelating agent is a pyrophosphate ion, more preferably from 0.01% to 1.35%, yet more preferably from 0.1% to 1%, by weight of the composition; and (d) pH greater than 8.3.

Another aspect of the invention provides a dentifrice composition comprising: (a) 20% to 75%, preferably 50% to 60%, of water by weight of the composition; (b) 0.0025% to 4.0%, preferably from 0.19% to 3.8% sodium monofluorophosphate by weight of the composition; (c) 0.001% to 4% calcium chelating agent by weight of the composition, preferably wherein the calcium chelating agent is a pyrophosphate ion, more preferably from 0.01% to 1.35%, yet more preferably from 0.1% to 1%, by weight of the composition; and (d) pH greater than 8.3. In one embodiment, the composition further comprises 25% to 60%, preferably 27% to 47%, of a calcium-containing abrasive by weight of the composition, preferably wherein the calcium-containing abrasive comprises calcium carbonate composition.

Another aspect of the invention provides a dentifrice composition wherein a monofluorophosphate ion degrades less than 40%, more preferably less than 35%, and more preferably less than 30% after 14 days at 60° C. relative to the monofluorophosphate ion in freshly prepared dentifrice composition. In one embodiment, the composition comprises a percentage of degraded monofluorophosphate ion that remains as free fluoride ion after 14 days at 60° C. is greater than 50%, or greater than 75%, preferably greater than 85%, more preferably greater than 90%. In another embodiment, the composition contains greater than 3,660 parts per million (ppm) monofluorophosphate ion after 14 days at 60° C., preferably from 4,000 ppm to 8,000 ppm of monofluorophosphate ion, more preferably from 5,000 to 7,000 ppm of monofluorophosphate ion, yet more preferably from 5,500 to 7,000 ppm of monofluorophosphate ion after 14 days at 60° C. In yet another embodiment, the composition contains greater than 3,260 parts per million (ppm) monofluorophosphate ion after 43 weeks at 30° C., preferably from 3,500 ppm to 11,000 pm of monofluorophosphate ion, more preferably greater than 4,000 ppm to 11,000 ppm, yet more preferably 5,000 ppm to 11,000 ppm, yet still more preferably from 6,000 ppm to 11,000 ppm monofluorophosphate ion after 43 weeks at 30° C. In still another embodiment, the calcium chelating agent is from 0.1% to less than 1.0% of a pyrophosphate salt by weight of the composition, preferably wherein the pyrophosphate is tetrasodium pyrophosphate.

In one embodiment, the dentifrice composition is a single phase composition.

These and other features, aspects, and advantages of the present invention will become evident to those skilled in the art from the detailed description which follows.

DETAILED DESCRIPTION OF THE INVENTION

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of" The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Calcium Chelating Agents

One aspect of the invention provides for the dentifrice compositions containing calcium chelating agents. In one embodiment, the calcium chelating agent is any pyrophosphate salt source. On such source for pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species.

Tetrasodium pyrophosphate salt is a preferred pyrophosphate salt in the compositions of the present invention. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt, useful for providing the improved monofluorophosphate ("MFP") delivery or maintenance of MFP species to enhance fluoride uptake, is from 0.01% to less than 1.5% by weight of the dentifrice composition, preferably from 0.1% to 1.4%, alternatively from 0.1% to 1.36%, more preferably from 0.2% to 1.2%, alternatively from 0.3% to 1.0%, alternatively from 0.1% to less than 1%, alternatively from 0.4% to 0.8%, alternatively combinations thereof, by weight of the composition. Any of the above mentioned pyrophosphate salts may be used. The pyrophosphate salts are described in more detail in Kirk-Othmer Encyclopedia of Chemical Technology, Third Edition, Volume 17, Wiley-Interscience Publishers (1982).

Water

The compositions of the present invention comprise herein from 45% to 75%, by weight of the composition of water. In one embodiment, the composition includes from 40% to 70%, alternatively from 45% to 65%, alternatively from 40% to 60%, alternatively from 50% to 70%, alternatively from 50% to 60%, alternatively from 45% to 55%, alternatively from 55% to 65%, alternatively from 50% to 60%, alternatively about 55%, alternatively combinations thereof, of water by weight of the composition. The water may be added to the formulation and/or may come into the composition from the inclusion of other ingredients. Preferably the water is USP water.

Calcium-Containing Abrasive

The compositions of the present invention comprise from 25% to 50% by weight of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In a preferred embodiment, the composition comprises from 25% to 60%, more preferably from 25% to 50%, even more preferably from 25% to 40%, yet even more preferably from 26% to 39%, alternatively from 27% to 47%, alternatively from 27% to 37%, alternatively from 30% to 35%, alternatively from 30% to 34%, alternatively combinations thereof, of a calcium-containing abrasive by weight of the composition.

In yet still a further preferred composition contains calcium-containing abrasive at the previously indicated weight percentage, wherein the calcium-containing abrasive is a calcium carbonate, and wherein the calcium carbonate has: a D50 particle size range from 2 microns to 7 microns, preferably from 3 microns to 6 microns, more preferably from 3.4 microns to 5.8 microns; or D90 from 8 microns to 15 microns, preferably from 9 microns to 14 microns, more preferably from 9.2 microns to 13.5 microns; or D98 range from less than 28 microns, preferably from 1 micron to less than 27 microns, more preferably less than 26 microns or from 1 micron to less than 26 microns. More preferably the calcium carbonate has a particle size range at the aforementioned D50 and D90 ranges; even more preferably at the aforementioned D50, D90 and D98 ranges. Surprisingly, it is believed that having calcium carbonate at these aforementioned particle size distribution ranges may increase fluoride stability benefits. Fluoride stability may be measured as described in herein, and generally China's National Standard Method GB8372-2008.

The term "D50" means, in particle size distribution measurements, the mass-median-diameter, considered to be the average particle size by mass. That is, the D50 is the size in microns that splits the distribution with half above and half below this diameter by mass. The term D90 similarly means the size in microns that splits 90 percent of the distribution below the D90 by mass. And the similarly the term D98 means the size in microns that 98 percent of the distribution below the D98 by mass.

The particle size of calcium carbonate (as a raw material) is measured by using a laser scattering particle sizing instrument (e.g., Bettersize BT9300H from DanDong Better Instrument, China). Generally, the laser scattering technique works by measuring the light diffracted from particulates as they pass through a laser beam. Particulates scatter light at an angle that is directly related to their size. Accordingly, the Bettersize BT9300H uses the light scattering pattern associated with a sample to calculate particle size distributions. The methods of ISO 13320-1-1999 are followed. Briefly, calcium carbonate raw material is pre-dispersed in deionized water (DI-water"). And a volume of calcium carbonate slurry is transferred to sampling cell, which is filled with DI-water as dispersion solution. The particles of calcium carbonate are well dispersed by re-circulation and ultrasonication while particle size measurements are being obtained.

In one embodiment, the calcium-containing abrasive is calcium carbonate. In a preferred embodiment, the calcium-containing abrasive is selected from the group consisting of fine ground natural chalk, ground calcium carbonate, precipitated calcium carbonate, and combinations thereof. In a more preferred embodiment, the calcium-containing abrasive is selected from fine ground natural chalk, ground calcium carbonate, and combinations thereof (at the aforementioned weight percentage ranges for calcium-containing abrasives; and having the aforementioned D50, D90, and D98 measurements).

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 µm and a BET surface area of 0.5 to 3 $m^2/g$. The natural calcium carbonate may have a particle size of 325 to 800 mesh, alternatively a mesh selected from 325, 400 600, 800, or combinations thereof; alternatively the particle size is from 0.1 to 30 microns, or from 0.1 to 20 microns, or from 5 to 20 microns.

In one embodiment, the composition of the present invention is free or substantially free of silicate.

PEG

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to less than 10%, yet more preferably from 0.5% to 7%, alternatively from 1% to 5%, alternatively from 0.5% to 10%, alternatively from 1% to 8%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula: $H-(OCH_2CH_2)_n-OH$. One supplier of PEG is Dow Chemical Company under the brand name of CARBOWAX™.

Sweetener

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Fluoride Ion Source

The compositions may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, and zinc fluoride. In one embodiment, the dentifrice composition contains a fluoride source selected from stannous fluoride, sodium fluoride, and mixtures thereof. In a preferred embodiment of the present invention, the fluoride ion source is sodium monofluorophosphate, and wherein the composition more preferably comprises 0.0025% to 2% of the sodium monofluorophosphate by weight of the composition, alternatively from 0.5% to 1.5%, alternatively from 0.6% to 1.7%, alternatively combinations thereof. In one embodiment, the dentifrice composition comprises from 1 parts per million (ppm) to 15,000 ppm, alternatively from 100 ppm to 8,000 ppm, alternatively from 5,000 ppm to 10,000 ppm, alternatively from 7,000 to 9,000 ppm, of monofluorophosphate (MFP) ion.

pH

The pH of the dentifrice composition may be greater than pH 7.8, preferably greater than pH 8.3, or from pH 8 to 13, or from pH 8.4 to 13, or more preferably from pH 9 to 12, alternatively greater than pH 8.5, alternatively greater than pH 9, alternatively from pH 9 to 11, alternatively from pH 9 to 10, or combinations thereof.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR#10010-772/Orion #8172BNWP; Epoxy body—VWR #34104-830/Orion #8165BN or VWR#10010-770/Orion #8165BNWP; Semi-micro, epoxy body—VWR #34104-837/Orion #8175BN or VWR#10010-774/Orion #3175BNWP; or (ii) Orion PerpHect combination: VWR #34104-843/Orion #8203BN semi-micro, glass body; or (iii)

suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not being used, the electrode is kept immersed in a pH 7 buffer solution or an appropriate electrode storage solution.

pH Modifying Agent

The dentifrice compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or "TSP"), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. In one embodiment, the dentifrice composition comprises: from 0.01% to 3%, preferably from 0.1% to 1% of TSP by weight of the composition; and from 0.001% to 2%, preferably from 0.01% to 0.3% of monosodium phosphate by weight of the composition. Without wishing to be bound by theory, TSP and monosodium phosphate may also have calcium ion chelating activity and therefore provide some monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. In one embodiment, the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the composition.

Thickening Agent

The dentifrice compositions herein may include one or more thickening agents. A thickening agent may be used in an amount from about 0.01% to about 15%, or from about 0.1% to about 10%, or from about 0.1% to about 5%, by weight of the composition. Non-limiting examples may include those described in US 2008/0081023 A1 at paragraphs 134 to 137, and the references cited therein.

In embodiment, the composition comprises a linear sulfated polysaccharide as a thickening agent. Carrageenans or carrageenans are one example of a linear sulfated polysaccharide. Generally, carrageenans can vary based upon the degree of sulfation that include: Kappa-carrageenan, Iota-carrageenan, and Lambda-carrageenan. Combinations of carrageenans can be used. In one embodiment, the composition contains from 0.1% to 3% of a linear sulfated polysaccharides by weight of the composition, preferably from 0.5% to 2%, alternatively from 0.6% to 1.8%, alternatively combinations thereof. In one embodiment, Iota-carrageenan is used.

In one embodiment, the composition comprises a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). In one embodiment, the composition comprising from 0.5% to 5% by weight of the composition of a silica agent, preferably from 1% to 4%, alternatively from 1.5% to 3.5%, alternatively from 2% to 3%, alternatively from 2% to 5%, alternatively from 1% to 3%, alternatively combinations thereof by weight of the composition.

In one embodiment, the composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A). In one embodiment, the composition contains from 0.1% to 3% of a CMC by weight of the composition, preferably from 0.5% to 2%, alternatively from 0.6% to 1.8%, alternatively combinations thereof by weight of the composition.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the composition comprises a thickener comprising: (a) 0.01% to less than 1.4%, preferably from 0.1% to 1.3%, more preferably from 0.5% to 1.3% of a carrageenan by weight of the dentifrice composition; and (b) greater than 0.4% to 2%, preferably from 0.5% to 1.8%, more preferably from 0.6% to 1.8% of a carboxymethyl cellulose (CMC) by weight of the dentifrice composition. In yet another embodiment, the aforementioned thickener further comprises 0.5% to 5%, preferably 1% to 4%, of a thickening silica by weight of the dentifrice composition.

Low or Free Humectants

The compositions herein may be substantially free or free of humectants, alternatively contain low levels of humectants. The term "humectant," for the purpose of present invention, includes edible polyhydric alcohols such as glycerin, sorbitol, xylitol, butylene glycol, propylene glycol, and combinations thereof. In one embodiment, the humectant is selected from sorbitol, glycerin, and combinations thereof. In yet another embodiment, the humectant is sorbitol. In one embodiment, the composition comprises from 0% to less than 20% of humectants by weight of the composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the composition. In yet another embodiment, the composition contains less than 20% of sorbitol by weight of the composition.

In an alternative embodiment, the compositions of the present invention comprise a humectant, preferably from 1% to 15% by weight of the composition.

Colorant

The compositions herein may include a colorant. Titanium dioxide is one example of a colorant. Titanium dioxide is a white powder which adds opacity to the compositions. Titanium dioxide generally can comprise from about 0.25% to about 5%, by weight of the composition.

Flavorant

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Data

Methods for assessing (i) free fluoride ion; (ii) monofluorophosphate "MFP" ion; (iii) soluble fluoride ion; (iv) fluoride uptake are described. Formulations of inventive Example 1 as well as Controls A-D are provided in Table 1. Lastly, data tables are provided showing the results of using the formulations of examples (as well as commercialized products) using the described methods. The superior results are achieved with the inventive composition.

A. Methods (i) Free Fluoride Ion

A method for assessing free fluoride ion (also known as ionic fluoride) in dentifrice is described. Free fluoride ion is measured by an ion-selected electrode (ISE). An example of a fluoride ion meter is from SARTORIUS PP-50. The meter may be fitted with a Fluoride-Specific ion electrode with Single-Junction Reference electrode. An example of such an electrode is from Orion Research, Inc., Cat. No. 9609BNWP. Equivalents of the meter and electrodes may also be used. The dentifrice sample for free fluoride assessment is prepared by using a balance that is accurate to the 0.0001 gram (g). 20 g of dentifrice is weighed into a tared 100 mL plastic beaker and then gradually 50 mL deionized water is added, while a magnetic stir bar is stirring in the plastic beaker, until the dentifrice is a completely disperse solution. The entire solution is gently transferred to a 100 mL plastic volumetric flask as to avoid generating foam (so the volume can be measured accurately), and deionized water is added to reach a total volume 100 mL, and then the solution is shaken manually to form a slurry. The formed slurry is then transferred into 10 mL centrifuge tubes, and centrifuged for 10 minutes at 15000 rotations-per-minute (RPM) (at 24149 g force) at ambient temperature. Thereafter 5 g of the resulting supernatant is weighed into a plastic container, 5 mL citrate buffer solution (described further below) is added to the same plastic container, and finally water is added until the total weight of the contents contained the container is 50 g. Thereafter, the 50 g of contents are mixed well (e.g., using a magnetic stir bar) in preparation for free fluoride measured by the aforementioned meter and electrode. The aforementioned citrate buffer solution is prepared by dissolving 200 g sodium citrate in a 2000 mL glass beaker, 120 mL glacial acetic acid, 120 g sodium chloride, and 60 g NaOH, all with deionized water until a total volume of about 1800 mL is achieved; and adjusting the pH to 5.0~5.5, and finally diluting the pH adjusted solution to a final volume of 2000 mL with deionized water.

Fluoride Ion working standards preparation is described. The fluoride standard curve is prepared as inputs, which is also used for ISE calibration on the fluoride ion test. A fluoride stock solution (~100 ppm) is prepared by weighing 0.1116 g NaF reference standard in a 100 mL polyethylene bottle. Water is added until the weight is 100 g. 10 g of this solution is then weighed out, with water added until a total weight of 50 g is achieved. Fluoride Ion standards are prepared by a Fluoride stock solution as described. The Fluoride stock solution (see table below for target weights) is weighed into individual tared 100 mL plastic bottles. Without re-taring the bottle, buffer solution is added to the bottle, and then water is weighed into the same bottle to obtain a total solution weight of approximately 50 grams. The resulting solution is mixed well.

| Target Concentration of $F^-$ Working Standards (ppm) | Weight of $F^-$ Stock Solution (g) | Volume of Buffer Solution (mL) | Total solution weight: stock solution + buffer + water (g) |
| --- | --- | --- | --- |
| 2 | 1.0 ± 0.005 | 5.0 | 50.0 ± 0.5 |
| 4 | 2.0 ± 0.005 | 5.0 | 50.0 ± 0.5 |
| 6 | 3.0 ± 0.005 | 5.0 | 50.0 ± 0.5 |
| 8 | 4.0 ± 0.005 | 5.0 | 50.0 ± 0.5 |
| 10 | 5.0 ± 0.005 | 5.0 | 50.0 ± 0.5 |
| 12 | 6.0 ± 0.005 | 5.0 | 50.0 ± 0.5 |

(ii) Monofluorophosphate (MFP) Ion

An Ion Chromatograph method is used to measure MFP ion levels in dentifrice. The Ion Chromatograph Instrument can be from DIONEX IC3000, fitted with an AS12A column and Guard 2 mm (P/N: 046055/046056); and AS14 column and Guard 4 mm (P/N: 046124/046134). The instrument is also fitted with a 2 mm and a 4 mm Anion Self-regenerator Suppressor (P/N: 064555, and P/N: 064554, respectively). Among the notable parameters used on the Ion Chromatograph Instrument are: (i) Injection size: 10 uL full loop injection; (ii) Eluent Flow: 2 mm AS12A: 0.4 mL/min; and 4 mm AS14: 1.0 mL/min; and (iii) Run Time of at least 16 minutes.

A dentifrice sample is prepared for MFP ion level assessment. A balance that is accurate to the 0.0001 gram (g) is used. 20 g of dentifrice is weighed into a tared 100 mL plastic beaker and then gradually 50 mL of deionized water is added, while a magnetic stir bar is stirring in the plastic beaker, until the dentifrice is a completely disperse solution. The entire solution is gently transferred to a 100 mL plastic volumetric flask as to avoid generating foam (so the volume can be measured accurately), and deionized water is added to reach a total volume of 100 mL, and then the solution shaken manually to form a slurry. The formed slurry is then transferred into 10 mL centrifuge tubes, and centrifuged for 10 minutes at 15000 rotations-per-minutes (RPM) (at 24149 g) at ambient temperature. Thereafter, 5 g of supernatant is weighed, and then an Eluent Preparation (2.0 mM $NaCO_3$ and 2.5 mM NaHCO$_3$) is added so that the total weight of supernatant and Eluent Preparation is 50 g, and then resulting solution is mixed well in a 100 plastic beaker. The mixed solution is filtered with a with 0.20 um nylon membrane (e.g., Millipore NYLON filter device, 0.20 um pores, Cat. No. SLGN033NB). The filtered solution is injected in either the AS12A or AS14 chromatography column for separation. Results are calculated based on monofluorophosphate standards.

MFP Ion stock preparation (~1000 ppm) is prepared by weighing 0.15 g of Sodium MFP into a 100 mL volumetric flask and adding water to a final weight of 100 g, and then mix well. Determine the actual concentration of the stock solution by using the formula listed below, (wherein the purity of the Sodium MFP raw material must be established prior to its use).

$$\text{ppm of MFP in Stock Solution} = \frac{(\text{gram of Na}MFP) * (\text{labeled purity of Na}MFP\ \%) * (0.68606) * 10^6}{\text{final weight (Na}MFP + \text{Water) g}}$$

The preparation of MFP working standards is described. The MFP stock solution (see table below for target weights) is weighed into individual tared 100 mL plastic bottles. Without re-taring the plastic bottle, eluent is added to the plastic bottle to obtain a total solution weight of approximately 100 grams, and the solution is mixed well.

| Approximate Concentration of MFP in working standard (ppm) | MFP Stock solution weight target (range) (g) | Total solution weight: stock solution + eluent (g) |
| --- | --- | --- |
| 1 | 0.10 ± 0.01 | 100.0 ± 0.5 |
| 5 | 0.50 ± 0.01 | 100.0 ± 0.5 |
| 10 | 1.00 ± 0.01 | 100.0 ± 0.5 |
| 25 | 2.50 ± 0.01 | 100.0 ± 0.5 |
| 50 | 5.00 ± 0.01 | 100.0 ± 0.5 |
| 75 | 7.50 ± 0.01 | 100.0 ± 0.5 |
| 100 | 10.00 ± 0.01 | 100.0 ± 0.5 |
| 150 | 15.00 ± 0.01 | 100.0 ± 0.5 |

(iii) Soluble Fluoride Ion

The method for assessing soluble fluoride ion is described consistently with the China's National Standard Method GB8372-2008. Briefly, an ion-selective electrode (ISE) is used to test soluble fluoride in dentifrice. An example of a fluoride ion meter is SARTORIUS PP-50, but an equivalent may be used. The ion meter may be fitted with a fluoride-specific ion electrode with a single-junction reference electrode by Orion Research Inc., Cat. No. 9609BNWP, but an equivalent may be used. The sample is prepared by using a balance that is accurate to the 0.0001 gram (g). 20 g of dentifrice is weighed into a tarred 100 mL plastic beaker and then gradually 50 mL of deionized water is added, while a magnetic stir bar is stirring in the plastic beaker, until the dentifrice is a completely disperse solution. The entire solution is gently transferred to a 100 mL plastic volumetric flask as to avoid generating foam (so volume can be measured accurately), and deionized water is added to reach a total volume 100 ml, and then the solution is shaken manually to form a slurry. The formed slurry is then transferred into 10 mL centrifuge tubes, and centrifuged for 10 minutes at 15000 rotations-per-minute (RPM) (at 24149 g force). Thereafter 0.5 mL of supernatant is transferred into a 2 mL mini-centrifugal tube, and 0.7 mL of 4 mol/L HCl is added to the tub. Then the tub is capped, heated in a 50° C. waterbath for 10 minutes. Thereafter the contents of the tub are transferred to a 50 mL measuring flask. The following are also added to the flask: 0.7 mL of 4 mol/L NaOH to neutralize the solution; 5 mL of citrate buffer solution; deionzed water is added until a total volume of 50 mL is achieved in the flask; and then the sample solution is gently mixed. The aforementioned citrate buffer solution is prepared by dissolving 100 g of sodium citrate, 60 mL of glacial acetic acid, 60 g of NaCl, and 30 g of NaOH, all with water, adjusting the pH to 5.0~5.5, and diluting the citrate buffer solution with deionized water until a total volume of 1000 mL is achieved. Turning back to the sample solution, the entire 50 mL solution is transferred to a 50 mL plastic beaker and the fluoride level is assessed based on a fluoride standard curve using the fluoride ion meter and electrode described.

The standard fluoride curve (w/w %) is prepared by accurately measuring 0.5 mL, 1.0 mL, 1.5 mL, 2.0 mL, and 2.5 mL fluoride ion standard solutions (100 mg/kg) into five respective 50 mL plastic measuring flasks. 5 mL of citrate buffer solution (made as previously described above) into each respective flask, and then diluting each solution to the scale with deionized water. Thereafter, each solution is transferred into a 50 mL plastic beaker respectively, measuring potential E under magnetic agitation, recording potential values, and drawing E-log c (wherein "c" is a concentration) standard curve.

(iv) Fluoride Uptake (i.e., Total Fluoride that is Bound within the Tooth Enamel).

The method for assessing Mean Fluoride Uptake is described. Enamel specimens are prepared by cutting 4 mm cores (chips) from extracted, human maxillary incisors using a diamond core drill. Chips are mounted in ¼ inch diameter Lucite rods (Beijing Mengzhijie M&E Engineering Technology Co., Ltd.) with dental acrylic (Shanghai New Century Dental Materials Co., Ltd.) covering all sides except the lingual surface. Course polishing of the surface with 600 grit silicon carbide-water slurry is used to remove approximately 50 microns of the outer enamel. Specimens are then polished for 30 minutes with gamma alumina (40-10076, BUEHLER) to a mirror finish. After sonicating and rinsing with deionized water, each chip is exposed to 25 mL of demineralization solution (0.025M/L lactic acid, 2×10-4 MHDP (MethaneHydroxy Diphosphonate), pH 4.5) for 32 hours at 23° C. for the formation of initial carious lesions. After removal from the demineralization solution, the chips are carefully rinsed in deionized water. Each chip is assessed through visual inspection (10× magnifications) to ensure enamel is free of surface imperfections. Chips are randomly placed into treatment groups (at 5 chips per treatment group). Early carious lesion with slight mineral loss is necessary for the fluoride uptake test to assess the absorption of the fluoride ion.

Dentifrice treatments are prepared by thoroughly mixing 8 grams of the subject dentifrice sample with 24 g of fresh pooled human saliva to form a slurry. The saliva is utilized within 2 hours of collection. Slurries are centrifuged for 10 minutes at 10,000 rotations per minute (12,096 g) and the supernatant removed. Each treatment group of specimens is exposed to 20 mL of supernatant for 30 minutes with constant stirring with a magnetic stir bar. Following the treatment, specimens are thoroughly rinsed with deionized water and then analyzed for fluoride content. A microdrill biopsy technique is used to assess each dentifrice sample's ability to deliver fluoride to the demineralized enamel. Specimens are mounted on the micro drill stage and sampled using a modified carbide dental bur. The biopsy technique removes a small portion of the chip, leaving behind a cylinder with the approximate dimensions 30-50 μm diameter and a constant 50 μm height. The powder removed is dissolved in 66.7 μl 0.5M HClO₄. Then buffered and pH adjusted with 133.4 μl Total Ionic Strength Adjustment Buffer (e.g., TISAB II) and 0.5N NaOH solution (1:1 value ratio) resulting in a final volume of 200 μl. Sample solutions are then analyzed by reading the millivolt potential with a fluoride ion specific electrode (Orion, Model 9609BNWP). Fluoride concentration is determined from a commercially available standard fluoride calibration curve obtained on the same day as the analysis and then calculated and averaged to obtain the Mean Fluoride Uptake.

B. Formulations

Table 1 below describes the formulary composition of inventive Example 1 and Control compositions 2 to 5 (Controls A to D, respectively). Notably, Example 1 has 1.10 wt % of sodium monofluorophosphate and 0.60 wt % of tetrasodium pyrophosphate and is at pH of 9.4. Controls (A, B, C) also have sodium monofluorophosphate (of varying levels), but no tetrasodium pyrophosphate and a pH lower than 9.4.

TABLE 2

|  | Ex 1 | | Control D - Ex 5 | |
| --- | --- | --- | --- | --- |
|  | MFP ion (ppm) | Soluble Fluoride Ion (ppm) | MFP ion (ppm) | Soluble Fluoride Ion (ppm) |
| Theoretical Level: | 7486 | 1450 | 7486 | 1450 |
| Fluoride Species at 60° C. for 14 days | 5610 | 1146 | 2050 | 610 |
| % drop (14 days vs. Theoretical) | 25% | 21% | 73% | 58% |
| Fluoride Species at 30° C. for 43 weeks | 6060 | 1272 | 2500 | 622 |
| % drop (43 weeks vs. Theoretical) | 19% | 12% | 67% | 57% |

Regarding Table 2, the term "theoretical level" is referring to the amount of MFP ion and Soluble Fluoride Ion calculated from a freshly prepared sample (i.e., the formulation having no opportunity for degradation). The intent of the shorter storage time period at higher temperature is to accelerate the equilibrium and any degradation kinetics. The data demonstrates that the presence of humectant (e.g., 16.8 wt % of sorbitol) in Control D may impact the results

TABLE 1

| Components: (Wt %) | Ex 1 | Ex 2 A | Ex 3 B | Ex 4 C | Ex 5 D | Ex 6 | Ex 7 | Ex 8 |
| --- | --- | --- | --- | --- | --- | --- | --- | --- |
| Total Water | 58.77 | 65.32 | 51.42 | 51.12 | 32.07 | 48.96 | 48.95 | 49.05 |
| Sorbitol | 0 | 0 | 0 | 0 | 16.8 | 0 | 0 | 0 |
| Sodium Monofluorophosphate | 1.1 | 0.8 | 0.8 | 1.1 | 1.1 | 1.1 | 1.1 | 1.1 |
| Sodium Monophosphate | 0.08 | 0 | 0 | 0 | 0.08 | 0.08 | 0.08 | 0.08 |
| Sodium Triphosphate | 0.42 | 0 | 0 | 0 | 0.42 | 0.42 | 0.42 | 0.42 |
| Tetrasodium Pyrophosphate | 0.60 | 0 | 0 | 0 | 0.01 | 0 | 0 | 0.5 |
| Sodium Saccharin | 0.25 | 0.48 | 0.48 | 0.48 | 0.25 | 0.58 | 0.58 | 0.58 |
| Sodium Carboxymethyl Cellulose | 0.91 | 0.4 | 0.4 | 0.4 | 1.32 | 0.9 | 1.32 | 1.32 |
| Carrageenan | 1.2 | 2 | 1.4 | 1.4 | 0 | 1.414 | 0 | 0 |
| Thickening Silica | 2.62 | 3 | 0.5 | 0.5 | 3 | 2.6 | 3.6 | 3 |
| Calcium Carbonate | 32 | 25 | 42 | 42 | 42 | 42 | 42 | 42 |
| Sodium Lauryl Sulfate | 1.1 | 2 | 2 | 2 | 2.1 | 1.1 | 1.1 | 1.1 |
| Methyl Paraben | 0.05 | 0 | 0 | 0 | 0 | 0 | 0 | 0 |
| Propyl Paraben | 0.05 | 0 | 0 | 0 | 0 | 0 | 0 | 0 |
| Flavor | 0.85 | 1 | 1 | 1 | 0.85 | 0.85 | 0.85 | 0.85 |
| Total: | 100 | 100 | 100 | 100 | 100 | 100 | 100 | 100 |
| pH | 9.4 | 7.8 | 8.3 | 8.3 | 8.8 | 9.4 | 9.2 | 9.4 |

C. Results

The data of Table 2 below assesses the monofluorophosphate (MFP) ion and soluble fluoride ion, on a parts-per-million (ppm) basis for Examples 1 and 5 (Control D) at an initial theoretical level and after 14 days at 60° C. temperature; and after 43 weeks at 30° C. Example 1 provided superior results compared to Example 5 given the lower percent drop of MFP ion and Soluble Fluoride ion at the 14 days and 43 week time points.

negatively. In one embodiment, the dentifrice composition of the present invention is free of polyol, especially glycerol or sorbitol.

Table 3 below assesses the free fluoride ion and monofluorophosphate (MFP) ion on a parts-per-million (ppm) basis of subject dentifrice formulation at the accelerated stability storage conditions (at 60° C. for 14 days). The term "theoretical level" is referring to the amount of MFP ion and elemental fluoride calculated from a freshly prepared sample (i.e., the formulation having no opportunity for degradation).

TABLE 3

|  | Unit: | Ex 1 | Ex 2 | Ex 3 | Ex 4 | Ex 5 | Control E |
|---|---|---|---|---|---|---|---|
| Sodium MFP | wt % | 1.1 | 0.8 | 0.8 | 1.1 | 1.1 | 1.1 |
| Equivalent to MFP | ppm | 7486 | 5680 | 5680 | 7486 | 7486 | 7486 |
| Equivalent to Fluoride | ppm | 1450 | 1100 | 1100 | 1450 | 1450 | 1450 |
| MFP ion after 60° C./14 days | ppm | 5610 | 2850 | 1970 | 3260 | 2050 | 3660 |
| Degraded MFP ion after 60° C./14days | ppm | 1876 | 2830 | 3710 | 4226 | 5436 | 3826 |
| % Degraded MFP ion | % | 25% | 50% | 65% | 56% | 73% | 51% |
| Amount Degraded Fluoride ion | ppm | 362 | 547 | 718 | 818 | 1052 | 740 |
| Free Fluoride Ion level after 60° C./14 days | ppm | 361 | 168 | 184 | 211 | 225 | 113 |
| % Degraded MFP ion remains as free fluoride ion | % | 99%[a] | 31% | 26% | 26% | 28% | 15% |

[a]Due to the measured method variation and assumed Theoretical total fluoride added vs. what actual this would account for the variation of the +/− 2% in the calculation.

Regarding Table 3, the MFP ion degradation for the inventive Example 1 is significantly lower vs. the other control examples. For Example 1 the MFP at accelerated storage conditions has 25% degradation, where as all other controls show greater than 50% degradation of MFP ion. Furthermore, the resultant degraded MFP ion in Example 1 is maintained predominantly as free fluoride ion, based on a mass balance of theoretical level vs. the measured free fluoride.

The calculation for "Amount of Degraded Fluoride Ion (as result of degraded MFP)" is provided:

$$\text{Total Fluoride Added} - \frac{(\text{Amount of } MFP \text{ ion measured})}{\text{Relative Molecular Mass of } MFP} * \text{Relative Molecular Mass of Fluoride}$$

The application of this equation is demonstrated for Example 1:

$$1450 \text{ ppm} - \frac{5610 \text{ ppm}}{98} * 19 =$$

$$362 \text{ ppm is the Amount of Degraded Fluoride Ion}$$

The "Percentage of Degraded MFP ion Remaining as Free Fluoride Ion" is provided: Measured Free Fluoride Ion/ Amount Degraded Fluoride Ion (from calculation above) *100%. Applying this second equation to Example 1 yields: (361/362)*100=99%. See Table 3 above.

Therefore, the predominant fluoride species of the degraded MFP ion in Example 1 is maintained as free fluoride ion (i.e., non-complexed fluoride). However, all other Example controls have both a significantly higher MFP degradation rate/percentage and the free fluoride ion of the degraded MFP is relatively low.

One aspect of the invention provides a dentifrice composition wherein the monofluorophosphate ion degrades less than 40%, more preferably less than 35%, and more preferably less than 30%, alternatively from 1% to 40%, alternatively from 5% to 30%, alternatively combinations thereof, after 14 days at 60° C. relative to the monofluorophosphate ion in freshly prepared dentifrice composition.

Another aspect of the invention provides a dentifrice composition wherein a percentage of degraded monofluorophosphate ion that remains as free fluoride ion after 14 days at 60° C. is greater than 50%, or greater than 75%, preferably greater than 85%, more preferably greater than 90%, alternatively greater than 95%, alternatively from 75% to 100%, alternatively from 80% to 99%, alternatively from 80% to 98%, alternatively combinations thereof.

Another aspect of the invention provides a dentifrice composition wherein the composition contains greater than 3,660 parts per million (ppm) monofluorophosphate ion after 14 days at 60° C., preferably from 4,000 ppm to 8,000 ppm of monofluorophosphate ion, more preferably from 5,000 to 7,000 ppm of monofluorophosphate ion, yet more preferably from 5,500 to 7,000 ppm, alternatively combinations thereof, of monofluorophosphate ion after 14 days at 60° C.

Another aspect of the invention provides a dentifrice composition wherein the composition contains greater than 3,260 parts per million (ppm) monofluorophosphate ion after 43 weeks at 30° C., preferably from 3,500 ppm to 11,000 pm of monofluorophosphate ion, more preferably greater than 4,000 ppm to 11,000 ppm, yet more preferably 5,000 ppm to 11,000 ppm, yet still more preferably from 6,000 ppm to 11,000 ppm, alternatively combinations thereof, monofluorophosphate ion after 43 weeks at 30° C.

Yet still another aspect of the invention provides for the use of a linear sulphated polysaccharide, preferably a carrageenan, to provide improved fluoride ion stability. Table 4 below demonstrates that a carrageenan containing dentifrice formulation is better at fluoride ion stability than two control formulations. Examples 6, 7 and 8 as described by the formulation components of Table 1, are briefly summarized. Example 6 contains Iota-carrageenan at 1.4 wt %. Example 7 and Example 8 formulations do not have any carrageenan. Example 6 and Example 8 formulations both have slightly more sodium carboxymethyl cellulose (CMC) and thickening silica than Example 6, but notably Example 8 also has tetra sodium pyrophosphate (TSPP).

TABLE 4

| | | Soluble Fluoride drop (ppm) | | |
|---|---|---|---|---|
| Example | Formula difference: | 60° C. 4 weeks | 60° C. 6 weeks | 30° C. 52 weeks |
| 6 | Iota-carrageenan (1.4 wt %) | 530 | 830 | 330 |
| 7 | No Carrageenan Tetrasodium Pyrophosphate | 888 | 988 | 688 |

TABLE 4-continued

| | | Soluble Fluoride drop (ppm) | | |
|---|---|---|---|---|
| Example | Formula difference: | 60° C. 4 weeks | 60° C. 6 weeks | 30° C. 52 weeks |
| 8 | Tetrasodium Pyro-phosphate No Carrageenan | 676 | 876 | 376 |

Referring to Table 4, the data takes into account possible fluoride ion stability effects of CMC, silica, and TSP. Given the lower soluble fluoride ion drop (ppm) of carrageenan-containing Example 6 at 4 weeks and 6 weeks at 60° C., as well as 30° C. for about one year (52 weeks), indicates that the carrageenan is providing improved fluoride ion stability in the described formulation as compared the control formulations. Example 8 does not contain carrageenan, but does contain tetrasodium pyrophosphate (TSPP).

Fluoride Uptake Results are provided in Tables 5a, 5b, and 5c across three different experiments.

TABLE 5a

| | Fluoride Uptake Results. | | | | | |
|---|---|---|---|---|---|---|
| Product | Fluoride Source (ppm) | pH | % Degraded MFP ion remaining as free fluoride ion | % Degraded MFP ion[a] | Mean Fluoride Uptake ± (SEM) | Stat. |
| Ex 1 | 1450 ppm F as Na-MFP | 9.4 | 99% | 25% | 6.42 ± 0.24 | A |
| Ex 5* | 1450 ppm F as Na-MFP | 8.8 | 28% | 73% | 4.57 ± 0.27 | B |
| Placebo | 0 ppm F | 9.4 | — | — | 3.00 ± 0.10 | C |

*Example 5 is Control D, notably containing 0.01% TSPP by weight of the composition.
[a]14 days at 60° C.

TABLE 5b

| | Fluoride Uptake Results. | | | | | |
|---|---|---|---|---|---|---|
| Product | Fluoride Source (ppm) | pH | % Degraded MFP ion that remains as free fluoride ion | % Degraded MFP ion[a] | Mean Fluoride Uptake ± (SEM) | Stat. |
| Ex 1 | 1450 ppm F as Na-MFP | 9.4 | 99% | 25% | 5.37 ± 0.09 | A |
| Ex 2 | 1100 ppm F as Na-MFP | 7.8 | 31% | 50% | 4.70 ± 0.08 | B |
| Ex 3 | 1100 ppm F as Na-MFP | 7.8 | 26% | 65% | 4.58 ± 0.16 | B |
| Ex 4 | 1450 ppm F as Na-MFP | 8.3 | 26% | 56% | 4.88 ± 0.16 | B |
| Placebo | 0 ppm F | 9.4 | — | — | 2.46 ± 0.10 | C |

[a]14 days at 60° C.

TABLE 5c

| | Fluoride Uptake Results. | | | | | |
|---|---|---|---|---|---|---|
| Product | Fluoride Source (ppm) | pH | % Degraded MFP ion that remains as free fluoride ion | % Degraded MFP ion[a] | Mean Fluoride Uptake ± (SEM) | Stat. |
| Ex 1 | 1450 ppm F as Na-MFP | 9.4 | 99% | 25% | 6.42 ± 0.24 | A |
| E* | 1450 ppm F as Na-MFP | 9.8 | 15% | 51% | 4.31 ± 0.31 | B |
| Placebo | 0 ppm F | 9.4 | — | — | 3.00 ± 0.10 | C |

*Control E, COLGATE Maximum Protection—(Code: EXP02152055BR12JH); containing tetrasodium pyrophosphate.
[a]14 days at 60° C.

As a result of maintaining the fluoride species whereby the degradation of the MFP ion species is significantly reduced, and those that ions that degraded remain predominantly as the free fluoride species (non-complexed) thus provide significant improved fluoride uptake performance evidenced by the superior results of inventive Example 1 compared to controls across three different experiments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition with improved fluoride ion stability comprising:
   (a) 25% to 60% of a calcium-containing abrasive by weight of the composition, wherein the calcium-containing abrasive comprises calcium carbonate;
   (b) 20% to 75% of water by weight of the composition;
   (c) 0.0025% to 4.0% of a sodium monofluorophosphate by weight of the composition;
   (d) from 0.1% to 0.8% of a calcium chelating agent by weight of the composition, wherein the calcium chelating agent is a pyrophosphate ion; and
   (e) an alkali pH where the pH is from 9 to 12;
   wherein the composition is substantially free of glycerin, propylene glycol, and sorbitol.

2. The composition of claim 1, wherein the composition comprises 27% to 47% of the calcium carbonate composition.

3. The composition of claim 2, wherein the calcium carbonate is selected from fine ground natural chalk, ground calcium carbonate, and combinations thereof, and wherein the calcium carbonate has a D50 from 2 microns to 7 microns.

4. The composition of claim 3, wherein an monofluorophosphate ion degrades less than 30% after 14 days at 60° C. relative to the monofluorophosphate ion in freshly prepared dentifrice composition.

5. The composition of claim 1, wherein an monofluorophosphate ion degrades less than 40% after 14 days at 60° C. relative to the monofluorophosphate ion in freshly prepared dentifrice composition.

6. The composition of claim 5, wherein a percentage of degraded monofluorophosphate ion that remains as free fluoride ion after 14 days at 60° C. is greater than 50%.

7. The composition of claim 6, wherein the composition contains greater than 3,660 parts per million (ppm) monofluorophosphate ion after 14 days at 60° C.

8. The composition of claim 7, wherein the composition contains greater than 3,260 parts per million (ppm) monofluorophosphate ion after 43 weeks at 30° C.

9. The composition according to claim 1, wherein calcium chelating agent is from 0.1% to less than 1.0% of a pyrophosphate salt by weight of the composition.

10. The composition according to claim 1, wherein the pyrophosphate is tetrasodium pyrophosphate.

11. The composition of claim 2, further comprising: 0.01% to 7% of a linear sulfated polysaccharide by weight of the composition, wherein the linear sulfated polysaccharide is a carrageenan; and 0.5% to 2% of a carboxymethyl cellulose by weight of the composition.

12. The composition according to claim 1, further comprising from 0.5% to less than 10% polyethylene glycol (PEG) by weight of the composition.

13. The composition according to claim 12, further comprising from 1% to 8% of polyethylene glycol (PEG) by weight of the composition, wherein the PEG is selected from a molecular weight range from PEG 200 to PEG 600.

14. The composition according to claim 13, further comprising 0.01% to 0.11% of a paraben by weight of the composition, wherein the paraben is selected from methyl paraben, propyl paraben, or combinations thereof.

15. The composition according to claim 1, wherein the water is from 50% to 60% by weight of the composition.

16. The composition according to claim 13, wherein the water is from 50% to 60% by weight of the composition.

17. A method of treating tooth enamel comprising the step of contacting teeth with the dentifrice composition according to claim 1.

18. A dentifrice composition with improved fluoride ion stability comprising:
(a) 25% to 60% of a calcium-containing abrasive by weight of the composition, wherein the calcium-containing abrasive comprises calcium carbonate;
(b) 45% to 70% of water by weight of the composition;
(c) 0.0025% to 4.0% of a sodium monofluorophosphate by weight of the composition;
(d) from 0.1% to 0.8% tetrasodium pyrophosphate by weight of the composition;
(e) 0.1% to 3% carrageenan by weight of the composition;
(e) an alkali pH where the pH from 9 to 12;
wherein the composition is substantially free of glycerin, propylene glycol, and sorbitol.

* * * * *